United States Patent [19]
McWilliams, Jr.

[11] 3,978,150
[45] Aug. 31, 1976

[54] CONTINUOUS PARAFFIN DEHYDROGENATION PROCESS

[75] Inventor: Frederick G. McWilliams, Jr., Palatine, Ill.

[73] Assignee: Universal Oil Products Company, Des Plaines, Ill.

[22] Filed: Mar. 3, 1975

[21] Appl. No.: 554,389

[52] U.S. Cl.............................. 260/683.3; 208/108; 208/171
[51] Int. Cl.²......................................... C07C 5/32
[58] Field of Search.................. 260/683.3; 208/108, 208/171, 210

[56] References Cited
UNITED STATES PATENTS

| | | |
|---|---|---|
| 3,754,051 | 8/1973 | Suzukawa et al................ 260/683.3 |
| 3,785,963 | 1/1974 | Boyd et al.......................... 208/171 |
| 3,795,607 | 3/1974 | Adams et al....................... 208/210 |
| 3,799,866 | 3/1974 | Leugemann .................. 260/683.68 |
| 3,838,038 | 9/1974 | Greenwood et al. .............. 208/108 |
| 3,838,039 | 9/1974 | Vesely et al. ...................... 208/108 |

Primary Examiner—Veronica O'Keefe
Attorney, Agent, or Firm—James R. Hoatson, Jr.; Robert W. Erickson; William H. Page, II

[57] ABSTRACT

Continuous operation and a high rate of conversion are obtained in a normal paraffin dehydrogenation process through the use of a moving bed non-fluidized reaction zone operated at a subatmospheric pressure. Quantities of catalyst are periodically removed from the reaction zone, passed through regeneration and reducing zones operated at superatmospheric pressures and returned to the top of a reaction zone.

5 Claims, 1 Drawing Figure

U.S. Patent   Aug. 31, 1976   3,978,150
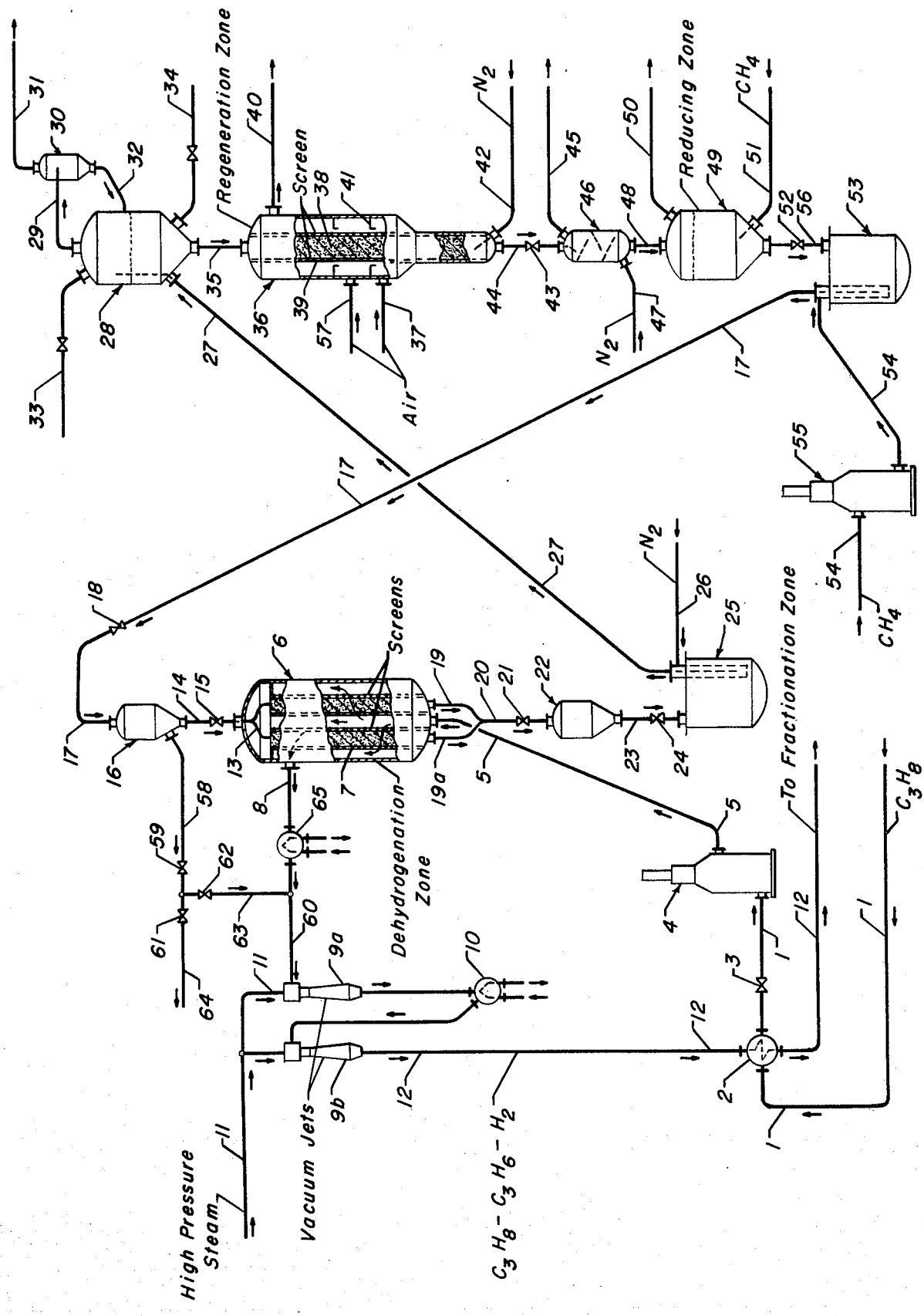

CONTINUOUS PARAFFIN DEHYDROGENATION PROCESS

FIELD OF THE INVENTION

The invention relates to a process for the catalytic dehydrogenation of saturated normal paraffins, especially those having from 2 to 6 carbon atoms per molecule. The invention also relates to the use of a moving bed reactor in a continuous dehydrogenation process operated at subatmospheric pressure and to the continuous removal, regeneration and replacement of catalyst.

PRIOR ART

The dehydrogenation of low molecular weight normal paraffins is an established commercial process. The basic method is often referred to as the "Houdry Process" and utilizes fixed beds of catalyst maintained at subatmospheric pressures. The catalyst rapidly becomes deactivated due to the deposition of carbonaceous substances on its surface. At this point, the reaction vessel is taken out of service and the catalyst is regenerated in situ. Multiple reactors are therefore utilized in order to provide continuous operation. This method requires relatively large capital expenditures for the reaction vessels and complex valving systems. Furthermore, the endothermic nature of the dehydrogenation reaction makes it necessary to supply large amounts of heat to a fixed bed operation by heating the feed stream above the temperature necessary to carry out the reaction.

The prior art has recognized these and other problems, and has developed fluidized processes in an attempt to overcome them. In these processes, fresh catalyst is continuously introduced into the reaction zone where it remains for only a short time before being separated from the reactants and transferred to a regeneration zone. This continuous catalyst turnover is also used to advantage to transfer heat into the reaction zone with the heated catalyst produced in a regeneration zone. These processes are described in U.S. Pat. Nos. 3,238,271, 3,284,161 and 3,342,561. A modification of this process is shown in U.S. Pat. No. 3,754,051 (Cl. 260-683.3), wherein the catalyst is heated by indirect heat exchange with a bed of particulate material warmed by a heating gas.

Moving bed reactors have been adapted to various hydrocarbon conversion processes. U.S. Pat. No. 2,303,717 presents a process having moving bed reaction and regeneration zones with intermediate catalyst stripping and storage. The more recent emphasis in this area has been concentrated in the field of naphtha reforming as shown by U.S. Pat. Nos. 3,761,390 (Cl. 208–65) and U.S. Pat. No. 3,838,038 (Cl. 208-108). Moving bed reactors have also been applied to residual oil desulfurization and demetallization (U.S. Pat. No. 3,795,607) and normal paraffin isomerization (U.S. Pat. No. 3,799,866).

BRIEF SUMMARY OF THE INVENTION

The invention provides a dehydrogenation process wherein the advantages of using a single reaction vessel, of performing continuous catalyst replacement, and of operating at a subatmospheric pressure are all obtained concurrently. A normal paraffin feed stream is passed through a non-fluidized bed of catalyst maintained at dehydrogenation conditions which include a subatmospheric pressure. Intermittently, relatively small quantities of catalyst are removed from the bottom of the catalyst bed, contacted with an oxygen-containing gas at a superatmospheric pressure to burn off carbon deposits and then contacted with a reducing gas to form active catalyst. Simultaneously, small quantities of the active catalyst are added to the top of the catalyst bed which flows by gravity downward through the reaction vessel.

DESCRIPTION OF THE DRAWING

The drawing illustrates one possible arrangement of a system adapted to the performance of the invention. The operation of the system will be described in terms of the dehydrogenation of propane, but this is not intended to limit the scope of the invention. A feed stream comprising propane enters the process through line 1 and is heated in feed-effluent heat exchanger 2. The feed stream then passes through a flow control valve 3 and enters a furnace 4. The feed stream is heated to the desired inlet temperature and passed through line 5 into a dehydrogenation reactor 6. The feed stream enters the central portion of the reaction zone, which is maintained at a subatmospheric pressure, and passes outwardly through an annular bed of catalyst 7. The contacting of the heated feed stream with the catalyst effects the dehydrogenation of a portion of the feed stream and the production of olefins and hydrogen. The olefins, hydrogen and unconverted propane exit the reaction zone through line 8 as the effluent stream of the process. Heat is recovered from the effluent stream in heat exchanger 65. The effluent stream is admixed with a smaller stream of methane passing at times through line 63 and is then passed into line 60. The effluent stream then enters the first of two vacuum jets 9a and 9b which are driven by high pressure steam entering through line 11. Interstage cooling is provided through heat exchange means 10. The effluent stream then passes through line 12 and the feed-effluent heat exchanger 2 to a fractionation zone for the recovery of the products. Unconverted propane may be recycled through line 1.

The useful life of the dehydrogenation catalyst is relatively short, and the catalyst within the reaction zone is gradually replaced with fresh catalyst to allow continuous operation of the process. Small discrete quantities of catalyst are withdrawn through a multitude of catalyst withdrawal lines represented by lines 19 and 19a and passed into a central collection line 20. The rate of catalyst withdrawal is controlled by valve means 21. The withdrawn catalyst falls into a collection hopper 22 wherein the catalyst is pressurized by a means not shown. The accumulated catalyst is then passed from the lock hopper 22 to a lift engager 25 through line 23 by opening valve means 24. Valve means 24 is once again closed and a gas stream comprising nitrogen or flue gas is passed through line 26 to cause the transfer of the catalyst upward through line 27.

The catalyst withdrawn from the reaction zone enters a collection hopper 28, and the catalyst is separated from the gas stream. The separated gases exit the top of the collection hopper through line 29 and enter into a cyclone separator 30. This results in a further separation of catalyst from the gases and produces an off-gas stream comprising fine catalyst particles which is removed in line 31. The larger reusable catalyst particles are returned to the collection hopper through line 32.

Fresh catalyst is added through line 33 to make up for breakage, and catalyst is removed through line 34 when a replacement or change of catalyst is desired.

Catalyst is withdrawn from the collection hopper 28 by gravity-flow through line 35. The catalyst then enters a regeneration zone 36 wherein it is retained as a dense cylindrical bed of catalyst 38 located within a screen 39. A first stream of air enters the regeneration zone through line 37 and is forced to pass upward through the catalyst bed 38 by the baffle means 41. A second stream of air enters through line 57 and also passes upward through the catalyst bed. Contacting of the hot catalyst with the air stream results in the burning off of the carbon layers on the catalyst. Excess air and the combustion products separate from the catalyst and are withdrawn through line 40. A small continuous stream of nitrogen enters the bottom of the regeneration zone through line 42 and is passed upward through the lower part of catalyst bed 38 to strip air from the catalyst.

Catalyst is withdrawn either intermittently or continuously through line 44 at a rate controlled by valve means 43. The catalyst then falls into a stripping vessel 46 wherein it is contacted by a second nitrogen stream entering through line 47. This nitrogen stream and the stripped gases are removed through line 45. The catalyst then falls through line 48 into a reducing zone 49. A small continuous stream of methane is fed into the bottom of the reducing zone through line 51. This results in the reduction of the metals contained on the catalyst. The gaseous effluent of the reducing zone is removed through line 50. The at least partially reduced catalyst is then removed from the reducing zone through line 56 at a rate controlled by valve 52 and passed into a second lift engager 53. A stream of methane entering the process through line 54 is passed through a second furnace 55, which heats it to a temperature substantially equal to that of the reaction zone. This gas stream is then passed into the lift engager to cause the transfer of the catalyst upward through line 17 and to insure its total reduction. The catalyst passes through a valve means 18 and enters an upper lock hopper 16. The heated methane passes downward through the catalyst and is removed via lines 58 and 64 through open valves 59 and 61. Valves 18 and 61 are then closed, and valve 62 in line 63 is opened to equalize the pressures within the lock hopper and within the reactor 6. Valve means 15 is then opened to allow the transfer of catalyst through lines 14 and 13 at a rate which is controlled by its withdrawal through lines 19a and 19.

DETAILED DESCRIPTION

Processes for the dehydrogenation of paraffins are operated to provide feed stocks for alkylation and polymerization processes. The fundamentals of the design and operation of a dehydrogenation plant are therefore known to those skilled in the art. Although a wide variety of processes have been developed to treat paraffins of different molecular weights or to best utilize different catalysts, the reaction zones used may be classified as being either a fluidized bed or a fixed bed. The fixed bed or "Houdry" units were developed first. The rapid deactivation of the catalyst normally experienced in a dehydrogenation process requires the use of at least two reactors, which can be operated and regenerated sequentially, in order to provide a continuous process. This necessitates a larger capital expenditure, both for the reactors and for the required multiplicity of large valves and process lines.

Dehydrogenation processes using a fluidized bed of catalyst in the reaction zone were therefore developed. Representative examples are described in U.S. Pat. Nos. 3,238,271; 3,284,161; 3,342,561; and 3,754,051. This process provides a means to obtain a rapid turnover of catalyst and therefore maintain a high and uniform catalyst activity within the reaction zone. It has a second advantage in that the catalyst is utilized as a heat transfer medium to carry the heat generated in the regeneration zone into the reaction zone. The endothermic nature of the dehydrogenation process may therefore be countered without heating the incoming feed stream to excessive temperatures.

The fluidized process is however not without its own problems or drawbacks, some of which are recognized in the above cited patents. One of the most serious disadvantages of a fluidized system is that it requires a superatmospheric pressure to allow its successful operation. The density and viscosity of the gaseous reactants is very low at a subatmospheric pressure, and the gases entering the reaction zone are therefore incapable of transporting sizable amounts of catalyst if a subatmospheric pressure is utilized. This places restraints on the operating conditions, such as the weight hourly space velocity (WHSV), which may be employed. Fluidized processes are therefore normally run at superatmospheric pressures. The major disadvantage of this is the deleterious effect it has on the equilibrium of the dehydrogenation reaction and therefore on the rate of dehydrogenation. It is therefore desirable from an equilibrium viewpoint to operate at a subatmospheric pressure as may be done on a fixed bed type of dehydrogenation process.

It is an objective of this invention to provide a process for the dehydrogenation of paraffins which allows continuous operation and continuous transfer of the catalyst into and from the reaction zone and which also allows operation at a subatmospheric pressure. That is, it is an objective of the invention to provide in one process different benefits obtainable from the fixed bed and fluidized modes of operation. This objective is achieved through the utilization of a moving bed reactor in the reaction zone. In such a reactor, the catalyst is confined to a dense, packed mass which is transferred downward solely by the action of gravity. There is therefore provided a continuous replacement of deactivated catalyst as in the fluidized processes, but without the necessity of fluidizing the catalyst and operating at a superatmospheric pressure.

The catalyst removed from the reaction zone is then stripped of combustible gases and regenerated by burning off carbon deposits in a separate zone which is preferably maintained above atmospheric pressure. This procedure also causes the oxidation of the metals contained in the catalyst. Contact of the hot highly oxidized catalyst with light hydrocarbons results in the reduction of the metals and the oxidation of the hydrocarbons. To avoid this destructive reaction from occurring to the feed stock, a relatively inexpensive reducing gas, such as methane or flue gas, is contacted with the catalyst in a separate reduction step prior to the return of the catalyst to the reaction zone.

The preferred embodiment of the invention may be characterized as a process which comprises the steps of passing a feed stream comprising saturated normal paraffins into a reaction zone maintained as dehydrogeration conditions including a temperature in excess of 1000°F. and a subatmospheric pressure, contacting the feed stream with a bed of dehydrogenation catalyst and effecting the formation of a reaction zone effluent stream comprising olefinic hydrocarbons and hydrogen, intermittently removing a quantity of used catalyst from the bottom of the bed of dehydrogenation catalyst and intermittently adding a quantity of active catalyst to the top of the catalyst bed and effecting a gradual movement of catalyst downward through the reaction zone, passing catalyst removed from the reaction zone into a regeneration zone operated at regeneration conditions which include the presence of an oxygen-containing gas stream and a superatmospheric pressure and effecting the production of regenerated catalyst, and passing regenerated catalyst into a reducing zone operated at reduction conditions which include the presence of a reducing gas and effecting the production of active catalyst which is added to the catalyst bed. The process of the invention is adaptable to the dehydrogenation of a broad range of paraffins having from 2 to 15 or more carbon atoms per molecule. Its utilization is therefore limited only by such factors as the ability to vaporize the heavier hydrocarbons and the excessive rates of coke formation which may result from the higher temperatures. It is preferred that the feed stream is formed by paraffins having from 2 to 6 carbon atoms per molecule.

The precise conditions used in the operation of the reaction zone will depend on many factors such as the relative activity of the catalyst, the composition of the feed stream, and the relative values placed on selectivity and the rate of conversion per pass. These latter factors will depend in turn on the market value of the products and by-products of the reaction and the capacity and efficiency of the downstream separatory systems. Dehydrogenation conditions in general are intended to include a subatmospheric pressure, a temperature of from 850° to 1500°F. and a WHSV of about 0.05 to about 5. Preferably, the pressure is in the range of from about 0.4 to 1.0 atmospheres, and the temperature is in the range of from about 1000°F. to about 1300°F. A higher temperature results in a higher reaction rate but also effects a larger variety of side reactions. Furthermore, at higher temperatures a larger amount of carbonaceous substances is deposited on the catalyst surface resulting in a higher rate of deactivation.

The preferred WHSV, defined as the mass of the feed stream passed over a specified volume of catalyst, will depend in part on the configuration chosen for the catalyst bed. A radial flow reactor would be operated differently than a plug flow reactor, that is a reactor containing a cylindrical bed of catalyst and having a vertical reactant flow. Radial flow reactors have the advantage of a low pressure drop because of their relatively large surface area and shallow bed depth. On the other hand, a plug flow reactor is more suited for use in a high space velocity-quick catalyst turnover situations and can be operated with a concurrent flow of the catalyst and the reactants. This allows increased transfer of heat into the reactor by the catalyst and ensures the contact of the reactants with active catalyst.

When a single pass radial flow reactor is utilized, it is preferred that the WHSV be in a lower range of from about 0.1 to about 0.5. In a single pass radial flow reactor, the reactants passing through all parts of the bed should contact relatively active catalyst. This dictates the usage of a relatively low WHSV to ensure that the catalyst in the bottom of the bed has not been deactivated during its residence within the reactor. A counter balancing factor is the desire to minimize the rate of catalyst movement to thereby minimize the rates of catalyst attrition and mechanical ware and to decrease the size of the regeneration system required. Therefore, the catalyst should be utilized to the fullest extent practical within the reactor before being subjected to the transfer and regeneration steps. In order to meet this goal and to ensure contact of the reactants with active catalyst, a multiple pass radial flow reactor is preferred. A multiple pass reactor possesses the additional advantage of allowing the use of inter-stage heating of the reactants to counteract the temperature decrease caused by passage through the previous beds of catalyst.

The dehydrogenation catalyst is preferably spherical in form and has a diameter of between one thirty-second and one quarter of an inch. A refractory base material such as alumina, silica-alumina or silica-magnesia may be used to form the spheres. The active catalytic material may be added in any of the known methods including coprecipitation or liquid impregnation by immersion of the spheres. One or more metals, such as nickel, iron or cobalt, chosen from Group VIII of the Periodic Table may be used. Especially preferred is a catalyst comprising chromium, vanadium or molybdenum, such as an alumina base promoted with chromium oxide. A great variety of other dehydrogenation catalysts have been developed, and further details may be obtained from such sources as U.S. Pat. Nos. 3,647,911; 3,679,773; 3,711,569; and 3,784,627.

The catalyst is transferred into and from the reactor proper through positive sealing valve means capable of maintaining the desired vacuum. To avoid pressure fluctuations during the actual transfer operation, lock hoppers are provided above and below the reactor. A second set of positive sealing valves is utilized to allow the evacuation of the lock hoppers and the equalization of the pressures within the lock hoppers and the reactor before the transfer is performed. This method of transfer is similar to that used in commercial moving bed reforming processes, such as described in U.S. Pat. Nos. 3,647,680 and 3,761,390, and the processes described in U.S. Pat. Nos. 3,838,039 and 3,795,607. The catalyst is preferably removed from the bottom of the reactor by a plurality of evenly distributed conduits designed as described in U.S. Pat. No. 3,785,963. This system provides a uniform withdrawal of catalyst through the different conduits to ensure an equal residence time for all portions of the catalyst bed. U.S. Pat. No. 3,856,662 provides a uniform solids withdrawal vessel which also functions as a lift engager wherein the catalyst is fluidized.

Due to the subatmospheric pressure maintained within the reaction zone, the catalyst withdrawal system utilized must differ from that employed in the above-cited moving bed reforming process and solids removal methods. These references utilize a high velocity gas stream to stop the flow of catalyst through the withdrawal conduits when the collection vessel is emptied. It is doubtful whether the desired subatmospheric pressure could be maintained during this procedure, and the flow through the withdrawal tubes is therefore controlled by a number of valve means in the withdrawal conduits or below the lock hopper.

Catalyst withdrawn from the reaction zone is purged by a stripping gas such as steam or nitrogen to limit the amount of combustible gas transferred into the regeneration zone. Likewise, active catalyst removed from the regeneration zone is stripped prior to passage into the reduction zone to limit the amount of oxygen-containing gas transferred with it. The regeneration and reduction zones are preferably located adjacent to the reaction zone as illustrated in the Figure. However, all three zones may be stacked, with the reaction zone being located either above or below the regeneration zone. In either case, the catalyst must be transported upward to the top of one of the zones. This may be performed by a bucket type continuous conveyor or by fluidization. It is preferred that fluidization is used since it requires few moving parts and also lends itself to simultaneous catalyst fine separation and catalyst treatment. In order to readily transport the catalyst by fluidization, this section of the process is maintained at atmospheric pressure or above. This higher pressure also decreases utility costs as it is not necessary to supply a vacuum source for all the gaseous streams passed into the regeneration and reduction zones.

Fines produced by the breakage of catalyst are removed before the catalyst is regenerated. This may be performed through the use of one or more cyclone type separators or by a system such as that described in U.S. Pat. No. 3,825,116. The retained catalyst is then passed into the regeneration zone, which is preferably designed in accordance with the teachings of U.S. Pat. No. 3,652,231, although the halogenation section thereof is not required. In the regeneration zone, the catalyst is contacted with gas streams having successively higher oxygen concentrations. The oxygen concentration and the rate of flow of the gas stream are controlled to produce a relatively high but still acceptable temperataure, since excessive temperatures cause the catalyst to sinter or are otherwise harmful. A portion of an oxygen poor flue gas is therefore often used as the first gas stream. The rapid rates of flow of the gas streams allow their use as heat sinks, and the generated heat may be recovered through heat exchange. The regeneration zone is operated at a lower temperature than in a fluidized process, and preferably at a temperature about 50° to 100°F. higher than the desired temperature in the reaction zone.

The rate of catalyst transfer in a moving bed process is not high enough to provide the total amount of heat required in the reaction zone. The feed stream is therefore heated to the reaction conditions, preferably by a direct fired heater after the feed stream has been heat exchanged against the effluent stream. In a low pressure system, the pressure drops caused by each part of the process should be minimized, and a heater with a low pressure drop, such as that described in U.S. Pat. No. 3,572,296, should be utilized.

The regenerated catalyst is then stripped of oxygen and passed into the reduction zone. In this zone, the metals on the catalyst are reduced from the high oxidation states resulting from their passage through the regeneration zone. This prevents the destructive oxidation of a portion of the feed stream, which would occur if the regenerated catalyst was passed directly into the reaction zone. The reduction zone is operated at a positive pressure substantially equal to or slightly above that maintained in the regeneration zone. Any gas flow is therefore from the reduction zone to the regeneration zone. The reducing gas may be any readily available and relatively inexpensive gas, such as a fuel-containing flue gas, a light off-gas from a stripping column or methane. The temperature in the reducing zone will be approximately the same as used in the regeneration zone. There will be some change due to the passage of the various gas streams through the zone, but the overall operation will essentially float on the temperature of the catalyst leaving the regeneration zone. The reduction zone may comprise several vessels, including the lift engager, transfer line and lock hopper above the regeneration zone as shown in the Figure.

The vacuum source is preferably one or more fluid jet ejectors but may be a mechanical system. Its location is set by a number of different factors, such as the low heat transfer coefficients for a subatmospheric gas in the feed-effluent heat exchanger, and the dilution and temperature reduction of the effluent possibly caused by the fluid used to compress the effluent. The ejector is preferably operated with the driving fluid inlet temperature and the pressure reduction or differential set to result in the ejector's effluent stream being cooler than the incoming reaction zone effluent stream. In this way, the ejector serves the dual purposes of evacuating the reaction zone and of quenching the reaction zone effluent. This quenching limits the undesired side reactions such as polymerization which occur in the hot effluent stream. The driving fluid used in the ejector may be either steam, a hydrogen-rich stream or a stream containing a vaporized hydrocarbon. The driving fluid should be one which does not increase the difficulty of isolating the olefinic product in the fractionation zone. It is preferred that a driving fluid other than steam be derived from the fractionation zone as the total number of required separation steps is thereby kept to a minimum. It is especially preferred that the driving fluid is comprised of mainly hydrogen and methane since these are readily separated from the higher molecular weight components of the reaction zone effluent stream.

The effluent stream is heat-exchanged for the recovery of heat and then passed into a separation system. It is preferred that the olefinic product is separated by fractionation, but other separatory methods may also be used. If adaptable to the process, a low pressure method has advantages. For instance, fractionation of low molecular weight hydrocarbons in the effluent requires the cooling and compression of the effluent, but it may be possible to separate the effluent at a subatmospheric pressure through the use of selective adsorbents and avoid much of the utilities cost of compression. A subatmospheric pressure separation zone also facilitates recycling uncoverted paraffins to the reaction zone.

Those skilled in the art will recognize the various different modes of operation which can be applied to the process. For instance, the regeneration and reduction zones may be fixed bed batch type operations rather than moving beds. With a large catalyst storage capacity available in the lock hopper feeding the reaction zone, the regeneration and reduction zones can be combined into one vessel in which the operations are performed in sequence. The reaction and regeneration zones may utilize either radial flow or plug flow through the catalyst bed, and the reaction zone may provide for both modes of operation. Furthermore, a plug flow reaction zone may be operated with either countercurrent or cocurrent flow of the catalyst and reactants.

I claim as my invention:

1. A catalytic dehydrogenation process which comprises the steps of:
   a. passing a feed stream comprising saturated normal paraffins into a reaction zone maintained at dehydrogenation conditions including a temperature in excess of 1000°F. and a subatmospheric pressure, contacting the feed stream with a bed of dehydrogenation catalyst and effecting the formation of a reaction zone effluent stream comprising olefinic hydrocarbons and hydrogen;
   b. intermittently removing a quantity of used catalyst from the bottom of the bed of dehydrogenation catalyst, and intermittently adding a quantity of active catalyst to the top of the catalyst bed, and effecting a gradual movement of catalyst downward through the reaction zone;
   c. passing catalyst removed from the reaction zone into a regeneration zone operated at regeneration conditions which include the presence of an oxygen-containing gas stream and a superatmospheric pressure and effecting the production of regenerated catalyst; and,
   d. passing regenerated catalyst into a reducing zone operated at reduction conditions which include the presence of a reducing gas and effecting the production of active catalyst which is added to the catalyst bed.

2. The process of claim 1 further characterized in that normal paraffins have from 2 to 6 carbon atoms per molecule.

3. The process of claim 1 further characterized in that the reaction zone is maintained at a subatmospheric pressure through the use of a fluid jet ejector, which ejector is operated with a temperature and a pressure differential which produces an expanded driving fluid having a lower temperature than the reaction zone effluent stream as it leaves the reaction zone, and admixing the expanded driving fluid with the effluent stream and effecting a reduction in the temperature of the effluent stream by passage through the fluid jet ejector.

4. The process of claim 3 further characterized in that the driving fluid used in the ejector comprises hydrogen and a vaporized hydrocarbon.

5. The process of claim 4 further characterized in that the driving fluid is derived from a stream removed from a fractionation zone in which the reaction zone effluent stream is separated.

* * * * *